United States Patent [19]

Hitzman

[11] 4,302,542

[45] Nov. 24, 1981

[54] FERMENTATION WITH THERMOPHILIC MIXED CULTURES

[75] Inventor: Donald O. Hitzman, Bartlesville, Okla.

[73] Assignee: Phillips Petroleum Co., Bartlesville, Okla.

[21] Appl. No.: 856,545

[22] Filed: Dec. 1, 1977

Related U.S. Application Data

[63] Continuation of Ser. No. 698,251, Jun. 21, 1976, abandoned.

[51] Int. Cl.$^3$ .................. C12N 1/32; C12N 1/20; C12R 1/01; A23J 1/00
[52] U.S. Cl. .................................. 435/247; 435/42; 435/253; 435/804; 435/822; 426/656
[58] Field of Search ............... 435/247, 244, 253, 804, 435/42, 822; 426/656

[56] References Cited

U.S. PATENT DOCUMENTS

| | | | |
|---|---|---|---|
| 3,655,510 | 4/1972 | Tanaka et al. | 435/110 |
| 3,764,474 | 10/1973 | Watanabe et al. | 435/248 |
| 3,767,534 | 10/1973 | Miura | 435/243 |
| 3,793,153 | 2/1974 | Miura | 235/249 |
| 3,981,774 | 9/1976 | Hitzman | 235/247 |
| 3,996,105 | 12/1976 | Harrison et al. | 435/42 |

FOREIGN PATENT DOCUMENTS 2407740 8/1974 Fed. Rep. of Germany .
7416644 7/1975 Netherlands .

OTHER PUBLICATIONS

Snedecor et al., "Thermophilic Mixed Culture of Bacteria Utilizing Methanol for Growth", *App. Microbiol.*, vol. 27, No. 6, (1974), pp. 1112–1117.

Brewersdorff, et al. "The Use of Methane for Production of Bacterial Protein", *Biotech Bioeng.*, vol. 13, (1971), pp. 119–162.

Hammer, et al., "Methane as a Source of Edible Material", *Eighth World Petroleum Congress Proceedings* vol. 5, (1971), App. Sci. Publishers Ltd., London, Eng., pp. 133–219.

*Primary Examiner*—Thomas G. Wiseman

[57] ABSTRACT

Single cell protein (SCP) and other fermentation products are produced by aerobic fermentation processes at relatively high fermentation temperature conditions employing oxygenated hydrocarbon compounds, such as an alcohol, as carbon and energy source material, and employing a unique thermophilic mixed culture of bacteria NRRL B-8158 as microbial conversion agent.

27 Claims, No Drawings

FERMENTATION WITH THERMOPHILIC MIXED CULTURES

This application is a continuation of Ser. No. 698,251, filed June 21, 1976, now abandoned.

FIELD OF THE INVENTION

The invention relates to the production of single cell protein. In another aspect, the invention relates to a novel thermophilic mixed culture.

BACKGROUND OF THE INVENTION

Efforts to relieve the impending worldwide shortages of protein have included various biosynthesis processes wherein biologically produced single cell protein (SCP) is obtained by the growth of a variety of microorganisms on a variety of carbon-containing substrates.

The carbon and energy sources used as substrates for such processes should be available widely, relatively cheap, uniform, and safe in that they do not leave harmful residues in the proteinaceous product ultimately obtained by the microbial conversions. Petroleum hydrocarbons have been employed as the carbon and energy source material, but have faced practical difficulties in the lack of water solubility, in the high consumption of oxygen to assist in the microbial conversion, and allegedly in traces of potentially carcinogenic agents from the petroleum feedstocks entering or adhering to the protein product.

Other processes have used oxygenated hydrocarbon derivatives as feedstocks due to the water solubility of such derivatives and hence ease of handling since microbial conversion processes are essentially conducted under aqueous conditions. Such feedstocks are readily available either from petroleum sources, natural gas sources, various waste/garbage processing and conversion of methane, and the like, from fermentation of various grains and the like, destructive distillation of wood, and so on. Such oxygenated hydrocarbons, whatever their source, are widely available and relatively cheap feedstocks for fermentation processes. Advantages accrue in that these feedstocks are partially oxygenated, so that substantially reduced molecular oxygen requirements are involved for the microbial conversion-growth process itself.

However, another difficult and limiting factor in the commercialization of single cell protein processes has been the necessity to conduct the fermentation at relatively moderate temperatures of about 20° to 50° C., and preferably not over about 35° C. Microbial conversions are exothermic oxidation reactions with large quantities of heat being produced. Heat must be removed from the fermentation admixture continuously and consistently, or risk the overheating of the system and either the death of the microorganisms or at least severe limitations of growth encountered as temperatures rise, and hence loss in efficiency.

Many processes have concentrated on the employment of one or other of the many available yeasts as the microorganism. Yeast cells generally are slightly larger than a bacteria cell, and sometimes provide easier separation from the fermentation process media.

However, bacteria offer advantages, since higher crude protein contents of the cell are obtained from bacteria as compared to the product obtainable from yeasts in general, since the yeasts have higher proportions of nonprotein structural material in their cells. Bacteria usually have a significantly higher true protein content, frequently being higher in the nutritionally important sulfur amino acids and lysine.

Discovery of bacteria with the capability of rapid growth and high productivity rates at relatively high fermentation process temperatures would be advantageous. High temperature growth operation means less heat to be removed, less cooling apparatus involved, and ultimately relatively smaller amounts of heat needed for sterilization, coagulation, and separation processes. Danger of contamination with other microorganisms is greatly reduced when high temperature fermentation can be employed. Thus, thermophilic or thermotolerant bacteria are definitely needed for commercialization of the single cell protein process.

SUMMARY OF THE INVENTION

I have discovered a unique thermophilic mixed culture of bacteria, containing three separate species of bacteria. These bacteria are individually classified as (1) a large gram-positive curved rod, division bacteria, class Schizomycetes, order Eubacteriales, family Bacillaceae, genus Bacillus; (2) a large gram-negative rod, division Bacteria, class Schizomycetes, order Eubacteriales, family Bacillaceae, genus Bacillus; (3) a short gram-negative rod, division Bacteria, class Schizomycetes. The mixed thermophilic culture exhibits highly desirable and useful properties. My $M_c$ mixed culture exhibits improved growth at higher temperatures than at conventional temperatures, producing higher cell yields, with reduced foaming tendencies under fermentation conditions.

My mixed culture is thermophilic, grows effectively with high productivity on oxygenated hydrocarbon feedstocks, particularly lower alcohols, most preferably methanol or ethanol, at temperatures wherein most other known bacteria species either are relatively unproductive, or simply cannot survive, or are unproductive and intolerant of an oxygenated hydrocarbon feedstock.

This unique mixed culture which I have discovered, and employ in my process, is designated as follows:

| Culture Name | My Strain Designation | Depository Designation |
|---|---|---|
| Mc | HTB-53 | NRRL B-8158 |

The designation NRRL B-8158 reflects the fact that I have deposited my thermophilic mixed culture with the official depository United States Department of Agriculture, Agricultural Research Service, North Central Region, Northern Regional Research Center, 1815 North University Street, Peoria, Ill. 61604, by depositing therewith thirty lyophilized preparations of my mixed culture, prior to filing of this application, and have received from the depository the NRRL designation B-8158 as indicated.

My unique mixed culture has been deposited in accordance with the procedures of the Department of Agriculture such that progeny of the mixed culture will be available during pendency of this patent application to one determined by the Commissioner of Patents and Trademarks to be entitled to access thereto in accordance with the Rules of Practice in Patent Cases and 35 U.S.C. 122. The deposit has been made in accordance with the practices and requirements of the United States Patent and Trademark Office such that all restrictions on availability to the public of progeny of the unique mixed culture will be irrevocably removed upon granting of a patent of which this important mixed culture is the subject, so that said culture will be available to provide samples for utilization in accordance with my invention. Thus, any culture samples from this deposit, or from cultures from which the deposit was derived, thus provide mixed culture strains derived from the thermophilic mixed culture of my discovery.

DETAILED DESCRIPTION OF THE INVENTION

I have discovered a peculiarly and uniquely effective thermophilic mixed culture of bacteria which I have designated as mixed strain HTB-53 and which has received U.S.D.A. depository designation NRRL B-8158. This mixed culture, for which I use the shorthand designation $M_c$, is a culture which is highly productive at relatively high fermentation temperatures, producing desirable and valuable single cell protein products with a high protein content of desirable amino acid type and balance.

My unique thermophilic mixed culture is compositionally stable. The mixed culture employed for lyophilization was isolated from a fermentation run and lyophilized under usual conditions which comprise rapidly freezing the microbial cells at a very low temperature followed by rapid dehydration under high vacuum, and storage at room temperature. To determine viability, some of the lyophilized samples were subsequently reactivated and subjected to growth of the lyophilized mixed culture under the same conditions utilized previously. The subsequent fermentations employing the reactivated $M_c$ culture gave essentially the same results in terms of high cell yield and the like, and apparent composition of the fermentation culture, as did the earlier runs. Microscopic examination of the reactivated $M_c$ culture indicated the same three organisms in the same form and relationship existing in the reconstituted culture as in the source fermentation.

This unique high temperature preferring culture provides improved rates of single cell protein production, with reduced cooling requirements, when grown on a carbon and energy substrate of an oxygenated hydrocarbon, preferably a lower alcohol, more preferably methanol or ethanol, and presently preferred is methanol or a substantially methanol-containing substrate.

There are distinct advantages in employing my unique thermophilic mixed culture $M_c$ in comparison to the utilization of a pure thermophile in the fermentation of methanol or of a similar carbon and energy source material. Firstly, a higher cell yield is obtained using the mixed culture. Cell yield as described herein is defined as the grams of cells produced per 100 grams of carbon and energy source material utilized, such as methanol. The higher cell yield is an important practical commercial enonomic advantage.

Another advantage for my unique thermophilic mixed culture in comparison to a pure thermophile, is the fact that foam generation is substantially less as compared to pure cultures which I have studied. Pure cultures generally tend to produce large amounts of foam during the fermentation process. While foam may be desirable in certain apparatus as a means of assisting in the fermentation process in heat transfer, and in assisting in providing the desired quantities of molecular oxygen for the aerobic fermentation process, nevertheless, many types of fermentation apparatus-means are not designed or equipped to handle excessive or large amounts of foam produced by some pure-strain microorganisms. Thus, the moderate amounts of foam produced by my unique culture are certainly a distinct advantage.

Another advantage for my unique mixed culture is the fact that the mixed culture inherently produces a single cell protein product which is a mixture of several varieties of cells, and thus the balance of amino acids in the recovered microbial cells from the $M_c$ is expected to have a more desirable balance than exhibited by the product of any single pure culture. A better amino acid balance simply means that there is less likelihood of a deficiency of a particular essential amino acid.

My unique thermophilic mixed culture was discovered by me during work to discover and develop a variety of cultures suitable for microbial conversion processes. A sample of soil was taken two feet below the surface of earth covering a steam line at the Bartlesville, Okla., Research Center of Phillips Petroleum Company. Conventional enrichment techniques in the presence of methanol were employed to isolate several separate or distinct cultures. During the course of the work in which several pure thermophilic cultures were isolated, it became apparent that a most unusual compositionally stable mixed culture of thermophilic organisms also had been obtained.

The thermophilic mixed culture which I have discovered is composed of three separate microorganisms. The three types of bacteria in my compositionally stable thermophilic mixed culture are described as (1) a large gram-positive curved rod, (2) a large gram-negative rod, and (3) a short gram-negative rod.

Repeated attempts at separation were made on this culture in order to isolate the pure microorganisms. For example, streak plates gave isolated colonies of the three organisms on a mineral agar media containing methanol. However, when the isolated colonies were transfered to aqueous media for further growth with methanol as the carbon and energy source material, surprisingly and unexpectedly no growth took place. Repeated efforts of this type were carried out, but without success.

The cooperative growth by this mixed culture indicates to me a symbiotic relationship between the three microorganisms. Theorizing, and without intending to be bound by such theorizing, but rather in an effort to help explain the relationship observed, it appears possible that a metabolic product or products of at least one of the microorganisms serves as a necessary substrate for the growth of one or other of the other microorganisms. While the exact nature of such a metabolite is not known at present, it appears possible that such metabolite may be toxic in nature to the microorganism which produces it, thereby explaining the need for the presence of the additional microorganism to consume this toxic metabolite in order for the first microorganism to continue to grow adequately.

A further indication of this symbiotic relationship that appears to exist between the three microorganisms making up my unique compositionally stable thermophilic mixed culture is the fact that fermentations employing my $M_c$ produce significantly less quantities of foam under typical aerobic fermentation conditions as compared to the quantities of foam normally observed under equivalent typical aerobic fermentation conditions but employing pure thermophilic bacteria Bacillus genus. This suggests to me, though again I do not wish to be bound by theorizing when I have discovered a unique mixed culture and have demonstrated how to employ it to obtain improved cell yields over that obtainable by pure strains, that my $M_c$ does not produce what would otherwise be expected in the way of very large amounts of foam during fermentation because in an $M_c$ fermentation an extracellular product, probably of proteinaceous nature, is being consumed by at least one of the symbiotic microorganisms, thereby continuously depleting such product as a foam-generating material in the fermentation admixture.

Carbon and Energy Source

The carbon and energy source material or substrate for the fermentation process of my invention employing my novel and unique mixed culture is an oxygenated hydrocarbon. The term oxygenated hydrocarbon is a generic term descriptive of the compounds employable, and not necessarily a limiting term referring to the source of the substrate. The oxygenated hydrocarbons include alcohols, ketones, esters, ethers, acids, and aldehydes, which are carbon-oxygen-hydrogen-containing water-soluble compounds and are substantially water-soluble in character. The oxygenated hydrocarbons preferably should be of up to about 10 carbon atoms per molecule for better water solubility, since higher molecular weights tend to reduce water solubility level.

Illustrative examples include: methanol, ethanol, propanol, butanol, pentanol, hexanol, 1,7-heptanediol, 2-heptanol, 2-methyl-4-pentanol, pentanoic acid, 2-methylbutanoic acid, 2-pentanol, 2-methyl-4-butanol, 2-methyl-3-butanol, 2-butanol, 2-methyl-1-propanol, 2-methyl-2-propanol, 2-propanol, formic acid, acetic acid, propanoic acid, formaldehyde, acetaldehyde, propanol, butanal, 2-methylpropanol, butanoic acid, 2-methylpropanoic acid, pentanoic acid, gluratic acid, hexanoic acid, 2-methylpentanoic acid, heptanedioic acid, heptanoic acid, 4-heptanone, 2-heptanone, octanoic acid, 2-ethylhexanoic acid, glycerol, ethylene glycol, propylene glycol, 2-propanone, 2-butanone, diethyl ether, methyl ethyl ether, dimethyl ether, di-n-propyl ether, n-propyl isopropyl ether, and the like, including mixtures of any two or more.

Petroleum gases, such as natural gas, such as methane, or other low carbon gases such as ethane and the like, can be oxidized to provide mixtures of predominantly the corresponding alcohols, as well as miscellaneous minor amounts of miscellaneous ketones, aldehydes, ethers, acids, and the like.

Among the oxygenated hydrocarbons, a presently preferred are the water-soluble alcohols as being suitable carbon and energy source materials for utilization by the thermophilic mixed culture of my discovery. Generally, these will be alcohols of 1 to 7 carbon atoms per molecule. Such alcohols include both linear and branched alcohols, primary, secondary, as well as tertiary. Such alcohols can be monohydroxy, as well as polyhydroxy.

Exemplary alcohol species include such as methanol, ethanol, propanol, butanol, pentanol, hexanol, 1,7-heptanediol, 2heptanol, 2-methyl-4-pentanol, 2-pentanol, 2-methanol-4-butanol, 2-methyl-3-butanol, 2-butanol, 2-methyl-1-propanol, 2-methyl-2-propanol, 2-propanol, glycerol, ethylene glycol, propylene glycol, and the like, including mixtures of any two or more.

The preferred alcohols are those of 1 to 4 carbon atoms per molecule, and most preferred are the monohydroxy alcohols, because of availability, water solubility, and economics. Methanol presently is an especially preferred alcohol because of its relatively low cost, wide availability, water solubility, and since governmental regulations on use are less cumbersome than with ethanol. Methanol also is readily obtainable by simple oxidative conversion of natural gas, which is primarily methane, and thus is or can be made readily available in many areas of the world which presently have surplus stocks of methane and little market for same, and correspondingly also sometimes have large populations of hungry people in this needlessly protein-deficient world.

A presently commercially available material sometimes termed "Methyl Fuel" (*C&EN*, Sept. 17, 1973, page 23) is exemplary of a commercially available mixture of methanol and controlled percentages of higher alcohols containing up to about 4 carbon atoms per molecule, and could be employed as a suitable substrate.

Fermentation Conditions

Since the fermentation process employing the thermophilic mixed culture in accordance with my invention is a process of aerobic fermentation, there must also be supplied adequate oxygen for the fermentation admixture. Aerobic fermentation processes basically are well known in the art, and means of supplying oxygen to fermentation admixtures are also well known. Generally, the supply of molecular oxygen to the aqueous fermentation reaction admixture can be provided by passing adequate volumes of air of ordinary oxygen content, or oxygen-enriched air if desired, or air and an augmented supply of such as pure oxygen separately, through the fermentation vessel. Offgases can be recovered, recycled if desired, for maximum utilization of oxygen, such as by stripping carbon dioxide from the offgases and recycing. In effect, using the oxygenated hydrocarbon as carbon and energy source substrate, a part of the oxygen demand needed for growth of the microorganism is supplied by the oxygen content of the substrate. Nevertheless, additional quantities of molecular oxygen must be supplied for suitable growth, since the assimilation of the substrate and corresponding growth of the microorganism is, in a sense, a combustion process. In general, exemplary is a range of about 0.1 and 10, more usually about 0.7 and 2.5, volumes per minute of air of normal oxygen content are supplied to the fermentation admixture per volume of aqueous liquid in the fermentor, or in terms of oxygen, the respective ranges would be about 0.02 to 2.1, and 0.14 to 0.55.

Pressures employed for my aerobic fermentation process can vary over a wide range. Exemplary would be considered a range of about 0.1 to 100 atmospheres (10.13–10,132 kPa), more usually from about 1 to 30 atmospheres (101.3–3,039 kPa), presently preferably about 1 to 5 atmospheres (101.3–506.5 kPa), as being suitable and convenient. Pressures greater than atmospheric pressure are advantageous in the process since such higher pressures tend to increase the dissolved oxygen content in the aqueous fermentation medium, which in turn tends to promote more rapid microbial growth. Pressures greater than atmospheric are especially useful employing my thermophilic mixed culture, since the higher temperatures employed in my thermophilic fermentation tend to decrease oxygen solubility in the aqueous fermentation medium admixture.

The culturing of my unique and novel $M_c$ mixed species of bacteria with the oxygenated hydrocarbon feedstock can be advantageously carried out at a temperature in the range of about 45° to 65° C., more preferably for optimum growth rates in accordance with my invention in the range of about 50° to 60° C. It should be noted that the temperature ranges given clearly indicate that the microorganisms utilized in my process are thermophiles in the accepted usage of the term, i.e., the microorganisms require such relatively high temperatures for suitable growth. Lower temperatures tend to inhibit (retard) growth rates.

High concentrations of some of the described carbon and energy source substrates, such as methanol, may be inhibitory to satisfactory microbial growth or even toxic to the microorganisms in the fermentations employing the mixed culture, and should be avoided.

The fermentation process can be carried out in a batch or in a continuous fashion, the presently preferred for economical SCP production is the growing of microbial cells in large quantities in a continuous process. A continuous process is particularly suitable when a carbon and energy source material is a lower alcohol, such as methanol or ethanol, which lends itself readily to controllable feed. The use of such microorganisms and the use of such feedstocks in a batch fermentation process is considered to be generally uneconomical on a practical basis. However, such substrates are conveniently utilized in a continuous fermentation process with overall high efficiencies and economies. In the fermentation, after the fermentor has been properly inoculated with the mixed culture species, the oxygenated hydrocarbon can be added as a separate stream, or admixed with water as an aqueous stream to sterilize same, or with mineral media to sterilize same, or any or all of these. Usually, it is fed separately for ease of control in the feed stream to the fermentor broadly in the range of about 2.5 to 35 weight percent, more usually and conveniently about 10 to 15 weight percent.

Culturing is accomplished in an aqueous growth medium comprising an aqueous mineral salt medium, the carbon and energy source material, molecular oxygen, and, of course, a starting inoculum of the $M_c$ mixed culture.

The fermentation growth rates can be adjusted by controlling the feed of oxygenated hydrocarbon. The feed rate of the carbon and energy source material should be adjusted so that the amounts being fed to the fermentor substantially are the same as the rate of consumption by the organism to avoid a significant buildup in the fermentor, particularly of any toxic materials which might inhibit the growth or even kill the microorganisms. A satisfactory condition usually can be exhibited by observation of little or no carbon and every feed material in the effluent being withdrawn from the fermentor, though a satisfactory check also can be obtained by watching the feed source material in the fermentor effluent so as to maintain at a desirable low level of about 0 to 0.2 weight percent.

Generally the retention time of microbial cells in the fermentor means in a continuous process is of the order on the average of about 2 to 4 hours under such conditions, though this is not critical and can vary widely.

The unique mixed culture $M_c$ of my discovery requires mineral nutrients and a source of assimilable nitrogen, in addition to the molecular oxygen, and the carbon and energy sources as described. The source of nitrogen can be any nitrogen-containing compound capable of releasing nitrogen in a form suitable for metabolic utilization by the organism. While a variety of organic nitrogen source compounds such as other proteins, urea, or the like, can be employed, usually inorganic nitrogen source materials are more economical and practical. Typically, such inorganic nitrogen-containing compounds include the presently preferred ammonia or ammonium hydroxide, as well as various other ammonium salts such as ammonium carbonate, ammonium citrate, ammonium phosphate, ammonium sulfate, ammonium pyrophosphate, and the like. Ammonia gas is convenient and can be employed by simply bubbling such through the gaseous fermentation media in suitable amounts.

The pH of the aqueous microbial fermentation admixture should be in the range, in accordance with my investigations, broadly from about 5.5 to 7.5, with a presently preferred range of about 6 to 7. Feed of the ammonia assists in controlling the pH desired, since otherwise the aqueous media tends to be slightly acidic. Of course, pH range preferences for microorganisms generally are dependent to some extent on the media employed, and thus the pH preference may change at least slightly with a change in mineral media, for example.

In addition to the oxygen, nitrogen, and carbon and energy source, it is necessary to supply selected mineral nutrients in necessary amounts and proportions to the feed media in order to assure proper microorganism growth, and to maximize the assimilation of the oxygenated hydrocarbon by the cells in the microbial conversion process.

A source of phosphate or other phosphorus, magnesium, calcium, sodium, manganese, molybdenum, and copper ions appear to provide the essential minerals. The recipe shown below can be used to culture my novel $M_c$ culture of my discovery. A mineral nutrient medium designated by me as FM-12 is useful in the fermentation process and is listed below along with the trace mineral solution which forms a part of the FM-12 nutrient medium:

| Component | Amount |
|---|---|
| FM-12 Medium | |
| $H_3PO_4$ (85%) | 2 ml |
| KCl | 1 g |
| $MgSO_4 \cdot 7H_2O$ | 1.5 g |
| $CaCl_2 \cdot 2H_2O$ | 0.2 g |
| NaCl | 0.1 g |
| Trace Mineral Solution | 5 ml |
| Distilled Water | To make 1 liter |
| Trace Mineral Solution | |
| $CuSO_4 \cdot 5H_2O$ | 0.06 g |
| KI | 0.08 g |
| $FeCl_3 \cdot 6H_2O$ | 4.80 g |
| $MnSO_4 \cdot H_2O$ | 0.30 g |
| $Na_2MoO_4 \cdot 2H_2O$ | 0.20 g |
| $ZnSO_4 \cdot 7H_2O$ | 2.00 g |
| $H_3BO_3$ | 0.02 g |
| $H_2SO_4$(conc.) | 3 ml |
| Distillerd Water | To make 1 liter |

Other mineral medium concentrations also can be employed, examples of which are provided in this disclosure in the Examples section.

In either a batch, or in the preferred continuous operation, all equipment, reactor or fermentation means, vessel or other container, piping, attendant circulating or cooling devices, and the like, should be sterilized, such as by the employment of steam such as about at least 250° F. for at least several minutes, such as about 15 minutes, prior to actual startup. The sterilized reactor then is inoculated with a culture from my mixed culture in the presence of all the required nutrients, and including the molecular oxygen and the oxygenated hydrocarbon feed.

In the fermentation process, as the culture begins to grow, the introduction of air or other molecular oxygen, nutrient medium, nitrogen source if added separately, and the alcohol or other oxygenated hydrocarbon, are maintained. The addition rate of the feed stream or streams can be varied so as to obtain as rapid a cell growth as possible consistent with the utilization of the carbon and energy source input, so that the objective of a maximized high yield cell weight per weight of feed charged is obtained. Of course, any of the feed streams can be added either incrementally or continuously as desired or convenient.

Instrumentation can be maintained to measure cell density, pH, dissolved oxygen content, oxygenated hydrocarbon concentration in the fermentor admixture, temperature, feed rates of input and output streams, and the like. It presently is preferred that materials fed to the fermentor be sterilized prior to introduction into the fermentor. When the oxygenated hydrocarbon is a material capable of sterilizing other materials, such as ethanol, or methanol, in some instances it may be convenient to add this component to other streams, such as the mineral media, in sterilizing amounts, and thus accomplish several purposes without the necessity for separate heat sterilization of the mineral media, for example, thus providing as maximum and economical an operation as possible. Heat added to any stream ultimately generally must be taken out by cooling means in the fermentor, since the aerobic fermentation is one in which heat is being produced.

The type of fermentor employed appears not to be critical in the practice of the fermentation process employing the mixed culture in accordance with my discovery. High productivity of the mixed culture with alcohol appears to be best achieved in a continuous process. Of course, watch must be maintained to control growth rates to avoid foam-out of the fermentor which could lower the effective liquid volume and cause some loss of fermentor contents. My unique mixed culture, has a distinct advantage, since while it is a "foamer", it is not an excessive foamer, and liquid levels can be more readily maintained in the fermentor without danger of foam-out. Particularly, addition of antifoam to the fermentation admixture is to be avoided, if at all possible, since antifoams such as the silicones may be detrimental to the dissolved oxygen content at the recommended high fermentation temperatures, and may cause organisms to grow at a slower rate, or even to die. The foam produced with my $M_c$ mixed culture is not harmful to growth, and definitely is beneficial in maintaining the organisms in a system of high dissolved oxygen content. Foam helps provide relatively large areas of gas/liquid contacting interfaces. Thus, fermentation can be improved and heat transfer improved as to control, uniformity, and avoidance of hot spots.

Of course, a foam-inducing substance such as some of the detergents, preferably nonionic, could be employed, if desired, to assist or induce additional foaming, though normally this is not necessary, or even desirable, with the $M_c$ mixed culture of my discovery.

Product Recovery

The recovery of microbial cells from my fermentation process can be accomplished by the usual techniques, such as acidification of fermentation effluent to a pH of such as about 4, and heating the acidified effluent to a temperature suitable to kill the microorganisms, such as about 80° C., though low enough not to damage the protein product. The effluent then can be centrifuged, washed, and recentrifuged to recover the microbial cells from the fermentor effluent. The cells can be treated to cause lysis to expedite recovery of protein and other materials from the cell. The fermentation also produces a number of desirable by-products which can be recovered from the fermentor effluent. These extracellular products can be economically helpful in the overall process, since they include valuable products such as polysaccharides, amino acids, such as glutamic acid, enzymes, vitamins, and the like.

The single cell protein product in accordance with my process, is a valuable source of protein for humans as well as for animals. For human consumption, the cells can be treated to reduce the nucleic acid content, if desired, though for animal feed purposes such treatment does not appear necessary.

EXAMPLES

Examples following are intended to be descriptive of runs employing the novel mixed culture of my discovery. Particular amounts and materials, or alcohols employed, should be considered as illustrative, not as limitative of my invention.

EXAMPLE I

A continuous fermentation run utilizing the thermophilic mixed culture of the instant invention was carried out. A 7 liter fermentor equipped with an aerator, stirrer, dissolved oxygen monitor, and means for measuring and controlling temperature and pH of the fermentation mixture, was charged with about 500 ml of fermentation reaction mixture from a previous fermentation run utilizing the thermophilic mixed culture, and 10 ml of methanol as the inoculant. The reactor also was charged with 2 liters of fermentation mineral medium FM-12.

The stirring rate was maintained at 1,000 rpm throughout the course of the run and the pH was controlled at from 6.2 to 6.35 by addition as necessary of ammonium hydroxide solution. Air was introduced into the fermentor at a rate of 2 liters per minute throughout the course of the run. At 6 hours into the run essentially pure oxygen also was introduced to the fermentor at a rate of 0.5 liters per minute, then was increased to 0.75 liters per minute at 118 hours, to 1.5 liters per minute at 174 hours and to 2 liters per minute at 190 hours during the run.

The medium continuously charged initially was the FM-12 medium previously described. At 22 hours, the mineral medium was changed to an aqueous composition of 7.5% by volume methanol in addition to the FM-12 medium plus 0.75 grams of potassium chloride, twice the normal trace mineral content, three times the normal manganese component content (all on a per liter basis), and with deletion of sodium chloride. At 166 hours, the feed was changed to an aqueous composition of 10% by volume methanol, 2.5 ml phosphoric acid (85%) per liter, 2 grams per liter potassium chloride, 1.75 grams per liter magnesium sulfate .7H$_2$O, 0.25 grams per liter of calcium chloride .2H$_2$O, 20 ml per liter of a manganese sulfate .H$_2$O aqueous solution (0.3 g/l), and 35 ml per liter of the trace mineral solution previously described.

The media feed rate during the run ranged from 700 ml per hour at 22 hours to 817 ml per hour at 118 hours, 781 ml per hour at 166 hours, and 763 ml per hour at 382 hours.

Samples of the fermentation effluent were withdrawn from time to time to recover the cells therefrom. Values obtained for cell content in terms of dry weight of cells in grams per liter and the yields calculated are presented below in Table I. Also shown in the table are values calculated for productivity in terms of grams of cells per liter per hour for the fermentation process.

At about 126 hours into the run, samples of the fermentation admixture were withdrawn and prepared for lyophilization of the microbial cells according to procedures known in the art. These lyophilized samples then were stored for subsequent use in a later fermentation run and for supplying samples of HTB-53 to a depository for microorganisms operated by the United States Department of Agriculture, Northern Regional Research Laboratory at Peoria, Ill.

Periodic samples also were taken from the fermentation reaction mixture for microscopic examination of the microbial cells in terms of their gross morphology. Such microscopic examination showed that the M$_c$ culture was composed of a large Gram positive curved rod, a large Gram negative rod, and a small Gram negative rod. Occasionally, a large Gram positive rod (not curved) also was observed, but this was believed to be a transitory variant of the large curved Gram positive rod.

TABLE I

| Time, Hours | 46 | 118 | 166 | 190 | 286 | 358 |
|---|---|---|---|---|---|---|
| Retention Time, Hours | 2.36 | 2.27 | 2.38 | 2.83 | 2.33 | 2.43 |
| Cells[a] g/l | 26.86 | 27.13 | 27.04 | 35.21 | 35.53 | 35.57 |
| Solids[b] g/l | 26.82 | 27.66 | 27.87 | 35.5 | 36.66 | 36.76 |
| Cell Yield[c] % | 44.7 | 46.1 | 46.47 | 44.4 | 45.8 | 45.9 |
| Productivity[d] g/l/hr | 11.4 | 12.2 | 11.7 | 12.5 | 15.7 | 15.1 |

[a]Value obtained by evaporating a 10 ml sample of fermenter effluent overnight at 100° C. and subtracting weight of mineral solids contained in 10 ml of medium.
[b]Value obtained by centrifuging 100 ml sample of fermenter effluent, resuspending solids in distilled water and centrifuging again to recover solids which are dried overnight at 100° C.
[c]Value obtained by dividing recovered solids (g/l) by methanol charged (g/l) × 100.
[d]Value obtained by dividing recovered solids (g/l) by retention time (hr).

EXAMPLE II

After about one month, a single tube of the lyophilized HTB-53 microbial culture from the fermentation run of Example I above was opened aseptically by conventional procedures and added to 100 ml of a fermentation medium designated IM2 which also contained 0.5% methanol. The composition of medium IM2 is shown below.

| IM2 Medium | |
|---|---|
| Component | Amount, g |
| KH$_2$PO$_4$ | 2.0 |
| K$_2$HPO$_4$ | 3.0 |
| MgSO$_4$ . 7H$_2$O | 0.4 |
| CaCl$_2$ . 2H$_2$O | 0.04 |
| NaCl | 0.1 |
| (NH$_4$)$_2$SO$_4$ | 2.0 |
| Trace Mineral Solution | 0.5 ml |
| Distilled Water | To make 1 liter |

The flask charged with the revived lyophilized culture was incubated with shaking at 55° C. After 24 hours, the shake flask showed good growth of the culture and 5 ml of the mixture was transferred to 100 ml of medium IM2 also containing 1.5% by volume methanol. Good growth developed within 24 hours and a third transfer was made to the same medium in two flasks, each containing 500 ml of IM2 medium plus 1.5% by volume methanol. This third transfer involved 100 ml of the culture being added to each of the two flasks. The culture was allowed to grow for 32 hours and then was utilized as the inoculant for a continuous fermentation run in the apparatus described above in Example I. The fermentor was charged with 1,000 ml of FM-12 medium, and 1,000 ml of the inoculant to which was added 10 ml of methanol. The temperature was maintained at 55° C., and the pH was controlled at from 6.25 to 6.4 by the continuous addition of ammonium hydroxide solution as before. Initially the stirrer was operated at 300 rpm, and air was introduced at a rate of 0.5 liters per minute, while the culture was permitted to establish itself in the fermentor. After 7 hours, a continuous introduction of feed media having the same composition as the last named feed media shown in Example I above was introduced. In addition, the air rate was increased to 2 liters per minute while the rpm was set at 1,000 for the stirrer. After 30 hours, the air rate was reduced to 1.75 liters per minute, while oxygen was introduced at 0.75 liters per minute, later increased to 1 liter per minute at 54 hours, and to 1.5 liters per minute at 198 hours. Again the fermentation effluent was sampled from time to time to provide data on the cell content in terms of grams per liter based on a dry weight and in terms of the yield and productivity of the fermentation. The data obtained during the run are presented below in Table II.

TABLE II[a]

| Time, Hours | 70 | 166 | 190 | 214 |
|---|---|---|---|---|
| Retention Time, Hours | 2.60 | 2.70 | 2.63 | 2.64 |
| Cells g/l | 34.33 | 33.56 | 33.87 | 34.84 |
| Solids g/l | 34.44 | 35.4 | 34.55 | 35.52 |
| Cell Yield % | 43.6 | 44.2 | 43.2 | 44.2 |
| Productivity g/l/hr | 13.2 | 13.1 | 13.1 | 13.5 |

[a]See footnotes for Table I above.

Samples of the microbial culture were also obtained during the fermentation run for microscopic examination as described in Example I. In this instance, there was also observed the large Gram positive curved rods and the large and small Gram negative staining rods. At 238 hours into the run, the culture was lost while attempting to change the feed to a higher alcohol concentration.

EXAMPLE III

Presented below in Table III are analytical data characterizing the microbial culture obtained in the run of Example I in terms of a chemical analysis of the microbial cells recovered. In Table IV there is also presented an amino acid content analysis of microbial cells recovered from another fermentation run utilizing the mixed thermophilic culture of my invention. For purposes of comparison, an amino acid content analysis of a pure thermophilic microorganism obtained during the course of the isolation of the thermophiles from the initial soil sample previously described is also presented in Table IV.

TABLE III

| Chemical Analysis of Microbial Cells Obtained in A Run HTB-53 | |
|---|---|
| Crude Protein[a], wt. % | 85.63 |
| Ash, wt. % | 9.19 |
| Amino nitrogen, wt. % | 13.4 |
| Carbon, wt. % | 44.7 |
| Hydrogen, wt. % | 6.79 |
| Nitrogen, wt. % | 13.7 |
| Phosphorous, wt. % | 1.71 |
| Potassium, wt. % | 0.91 |
| Magnesium, wt. % | 0.26 |
| Calcium, wt. % | 0.1 |
| Sodium, wt. % | <0.01 |
| Iron, ppm | 1300 |
| Zinc, ppm | 55.8 |
| Manganese, ppm | 126 |
| Copper, ppm | 20 |

[a]Nitrgoen content (13.7) × 6.25.

TABLE IV

Amino Acid Content of Thermophilic Cultures Grown on Methanol: Grams Per 100 Grams Product

| Essential Amino Acids | Pure (HTB-7) | Chem. Score[1][2] Values | Mixed (HTB-42) | Chem. Score[1] Values |
|---|---|---|---|---|
| leucine | 5.37 | 75 | 5.76 | 104 |
| isoleucine | 4.56 | 83 | 4.90 | 118 |
| lysine | 5.54 | 96 | 5.67 | 141 |
| methionine | 1.50 | 34 | 1.22 | 36 |
| cystine | * | | * | |
| threonine | 2.95 | 90 | 2.79 | 88 |
| phenylalanine | 2.68 | 80 | 2.78 | 88 |
| tyrosine | 2.55 | | 2.72 | |
| tryptophan | 0.60 | 43 | 0.89 | 90 |
| valine | 5.13 | 91 | 5.46 | 121 |

| Non Essential Amino Acids | Pure (HTB-7) | Chem. Score[1][2] Values | Mixed (HTB-42) | Chem. Score[1] Values |
|---|---|---|---|---|
| alanine | 5.65 | | 6.19 | |
| arginine | 3.39 | | 3.01 | |
| aspartic acids | 6.50 | | 6.26 | |
| glycine | 3.71 | | 4.19 | |
| glutamic acid | 10.47 | | 10.69 | |
| histidine | 1.26 | | 1.22 | |
| proline | 2.32 | | 2.38 | |
| serine | 2.09 | | 1.75 | |
| Total Essential amino Acids | 30.88 | | 32.19 | |
| Total Amino Acids | 66.27 | | 67.88 | |
| Crude Protein | 85.63 | | 84.4 | |

(* = not detected)
[1]Chemical Score Values: based on essential amino acid content of egg as 100 for same weight of protein.
[2]Based on averages from five pure thermophile runs.

It can be noted that the percentage of total amino acids which are essential amino acids is slightly higher for the mixed culture product (47%) than for the pure culture product (46%). Futhermore, if the essential sulfur-containing amino acids are supplied by addition of synthetic methionine, which is very likely since essentially all SCP's have been found to be low in these amino acids, the Chemical Score values show that the mixed culture product is twice as good from a nutritional standpoint as the pure culture product based on the next lowest essential amino acid Chemical Score value.

The disclosure, including data, illustrate the value and effectiveness of my invention. The examples, knowledge and background of the field of the invention, general principles of microbiology, chemistry, and other applicable sciences, have formed the bases from which the broad descriptions of my invention, including the ranges of conditions and generic groups of operant components have been developed, which have formed the bases for my claims here appended.

I claim:

1. A method of producing a single cell protein material which comprises culturing a mixed culture of thermophilic bacteria species microorganisms NRRL B-8158 in aqueous medium employing an oxygenated hydrocarbon as carbon and energy source under aerobic fermentation conditions at a fermentation temperature of at least about 45° C., and recovering the resulting microorganisms as a single cell protein material.

2. A process for the production of microbial cells which comprises aerobically culturing under thermophilic fermentation conditions at a fermentation temperature in the range of about 45° to 65° C. a strain of mixed thermophilic bacteria derived from a mixed culture deposited as NRRL B-8158 in a culture medium containing at least one oxygenated hydrocarbon as a primary carbon and energy source, nutrients, and a nitrogen source.

3. The process according to claim 2 comprising the further step of separating and recovering said microbial cells so produced from said culture medium.

4. The process according to claim 3 wherein said oxygenated hydrocarbon is characterized as a water-soluble alcohol, ketone, ester, ether, acid, aldehyde, or mixture, containing up to about 10 carbon atoms per molecule.

5. The process according to claim 4 wherein said oxygenated hydrocarbon is methanol, ethanol, propanol, butanol, pentanol, hexanol, 1,7-heptanediol, 2-heptanol, 2-methyl-4-pentanol, pentanoic acid, 2-methylbutanoic acid, 2-pentanol, 2-methyl-4-butanol, 2-methyl-3-butanol, 2-butanol, 2-methyl-1-propanol, 2-methyl-2-propanol, 2-propanol, formic acid, acetic acid, propanoic acid, formaldehyde, acetaldehyde, propanol, butanal, 2-methylpropanol, butanoic acid, 2-methylpropanoic acid, pentanoic acid, glutaric acid, hexanoic acid, 2-methylpentanoic acid, heptanedioic acid, heptanoic acid, 4-heptanone, 2-heptanone, octanoic acid, 2-ethylhexanoic acid, glycerol, ethylene glycol, propylene glycol, 2-propanone, 2-butanone, diethyl ether, methyl ethyl ether, dimethyl ether, di-n-propyl ether, n-propyl isopropyl ether, or mixture of any two or more.

6. The process according to claim 4 wherein said oxygenated hydrocarbon comprises a monohydric or polyhydric alcohol of 1 to 7 carbon atoms per molecule.

7. The process according to claim 6 wherein said alcohol is methanol, ethanol, propanol, butanol, pentanol, hexanol, 1,7-heptanediol, 2-heptanol, 2-methyl-4-pentanol, 2-pentanol, 2-methyl-4-butanol, 2-methyl-3-butanol, 2-butanol, 2-methyl-1-propanol, 2-methyl-2-propanol, 2-propanol, glycerol, ethylene glycol, propylene glycol, or mixture of any of these.

8. The process according to claim 6 wherein said alcohol contains 1 to 4 carbon atoms per molecule, and is methanol, ethanol, a propanol, or a butanol.

9. The process according to claim 8 wherein said alcohol comprises predominantly methanol or ethanol.

10. The process according to claim 9 wherein said culturing is conducted at a fermentation temperature in the range of about 50° C. to 60° C., and said alcohol comprises methanol.

11. The process according to claim 10 wherein the culture medium is maintained at a pH in the range of about 5.5 to 7.5.

12. The process according to claim 11 wherein said pH is maintained in the range of about 6 to 7.

13. The process according to claim 12 wherein said fermentation conditions are maintained so that the amount of methanol in the fermentor means effluent is in the range of 0 to 0.2 weight percent.

14. The process according to claim 13 wherein said aerobic culturing of said mixed culture includes fermentation conditions employing about 0.02 to 2.1 volumes of oxygen per minute per volume of liquid in said culture medium, and said culture medium is maintained under pressure of about 0.1 to 100 atmospheres.

15. The process according to claim 14 wherein said culturing is conducted under foam culture fermentation conditions.

16. The process according to claim 14 wherein said microbial cells are subjected to lysis.

17. The protein material prepared by the process which comprises culturing a mixed culture of bacterial microorganisms species NRRL B-8158 in an aqueous medium employing an oxygenated hydrocarbon as carbon and energy source under aerobic fermentation conditions at a fermentation temperature of at least about 45° C. and recovering from the resulting single cell microorganisms a protein material.

18. The protein material prepared by the process which comprises aerobically culturing, under thermophilic aerobic fermentation conditions in fermentation means at a fermentation temperature in the range of about 45° C. to 65° C., a strain of mixed bacteria derived from NRRL B-8158 in an aqueous culture medium containing at least one oxygenated hydrocarbon as a primary carbon and energy source, mineral nutrients, and an assimilable nitrogen source, thereby preparing single cell microbial cells, and recovering therefrom a protein material.

19. The protein material according to claim 18 wherein said oxygenated hydrocarbon contains up to about 10 carbon atoms per molecule.

20. The protein material according to claim 19 wherein said oxygenated hydrocarbon comprise a monohydric or polyhydric alcohol of 1 to 7 carbon atoms per molecule.

21. The protein material according to claim 19 wherein said alcohol is selected from the group consisting of methanol, ethanol, propanol, butanol, pentanol, hexanol, 1,7-heptanediol, 2-heptanol, 2-methyl-4-pentanol, 2-pentanol, 2-methyl-4-butanol, 2-methyl-3-butanol, 2-butanol, 2-methyl-1-propanol, 2-methyl-2-propanol, 2-propanol, glycerin, ethylene glycol, propylene glycol, and mixture of any two or more of these.

22. The protein material prepared according to claim 20 wherein said alcohol contains 1 to 4 carbon atoms per molecule, and is methanol, ethanol, a propanol, or a butanol, wherein said culturing is conducted at a fermentation temperature in the range of about 50° C. to 60° C., and wherein the culture medium is maintained at a pH in the range of about 5.5 to 7.5.

23. The protein material prepared according to claim 22 wherein said alcohol comprises predominantly methanol, and wherein said pH is maintained in the range of about 6 to 7.

24. The protein material prepared according to claim 23 wherein said fermentation conditions are maintained so that the amount of methanol in the fermentor means effluent is in the range of 0 to 0.2 weight percent.

25. The protein material prepared according to claim 24 wherein aerobic culturing of said mixed culture includes fermentation conditions employing about 0.02 to 2.1 volumes of oxygen per minute per volume of liquid in said culture medium, and said culture medium is maintained under pressure of about 0.1 to 100 atmospheres and a temperature of about 50° C. to 60° C.

26. The protein material prepared according to claim 18 wherein said recovering of said microorganisms so produced from said culture medium comprises a treating step effective to kill the microorganisms without substantial harm to the protein thereof, and a separation step separating microorganisms from said culture medium.

27. The protein material prepared according to claim 26 wherein said recovering comprises the steps of acidifying the culture media containing the microbial cells to a temperature effective to kill the cells without substantial harm to the protein thereof, centrifuging, washing, and effectuating lysis.

* * * * *